United States Patent [19]
Shepard

[11] Patent Number: 6,159,706
[45] Date of Patent: Dec. 12, 2000

[54] APPLICATION OF ENZYME PRODRUGS AS ANTI-INFECTIVE AGENTS

[75] Inventor: H. Michael Shepard, Rancho Santa Fe, Calif.

[73] Assignee: NewBiotics, Inc., San Diego, Calif.

[21] Appl. No.: 09/215,688

[22] Filed: Dec. 18, 1998

Related U.S. Application Data

[60] Provisional application No. 60/068,703, Dec. 23, 1997.

[51] Int. Cl.[7] .............................. C12Q 1/18; C12Q 1/26; C07D 5/00; A61K 38/00; A61K 31/43
[52] U.S. Cl. .............................. 435/32; 435/30; 435/43; 435/6; 435/2; 424/9.1; 530/300; 530/335; 514/16; 514/18; 514/199; 514/206; 514/204; 514/203; 514/246; 540/222; 540/225
[58] Field of Search .............................. 435/2, 6, 43, 32, 435/30; 424/9.1, 16.18; 514/199, 206, 204, 203, 246; 530/335, 300; 540/222, 225, 227; 544/21; 542/418

[56] References Cited

U.S. PATENT DOCUMENTS

| | | | |
|---|---|---|---|
| 4,297,488 | 10/1981 | Christensen et al. | 544/21 |
| 5,549,974 | 8/1996 | Holmes . | |
| 5,639,603 | 6/1997 | Dower et al. . | |
| 5,679,773 | 10/1997 | Holmes . | |

FOREIGN PATENT DOCUMENTS

| | | |
|---|---|---|
| 0 317 956 A2 | 5/1989 | European Pat. Off. . |
| 0 484 870 A2 | 5/1992 | European Pat. Off. . |
| 0 302 473 B1 | 2/1995 | European Pat. Off. . |
| 0 742 015 A1 | 11/1996 | European Pat. Off. . |
| 0 745 390 A2 | 12/1996 | European Pat. Off. . |

OTHER PUBLICATIONS

Boisvert, W. et al., "Mechanisms of Action of Chloroalanyl Antibacterial Peptides" *J. Biol. Chem.* 261(17):7871–7878 (1986).

Huber, B.E. and Richards, C.A., "Regulated Expression of Artificial Chimeric Genes Contained in Retroviral Vectors: Implications for Virus Directed Enzyme Prodrug Therapy (VDEPT) and Other Gene Therapy Applications" *J. Drug Targeting* 3:349–356 (1996).

Kerr, D.E. et al., "Regressions and cures of melanoma xenografts following treatment with monoclonal antibody β–lactamase conjugates in combination with anticancer prodrugs" *Cancer Res.* 55(16):3558–3563 (1995).

Maher, M. et al., "The sensitive detection of fluorescently labelled PCR products using an automated detection system" *Mol. Cell. Probes* 9:265–276 (1995).

Melton, R.G. and Sherwood, R.F., "Antibody–Enzyme Conjugates for Cancer Therapy" *J. Natl. Cancer Inst.* 88(3/4):153–165 (1996).

Meyer, D.L. et al., "Preparation and characterization of a β–lactamase–Fab' conjugate for the site–specific activation of oncolytic agents" *Bioconjugate Chem.* 3(1):42–48 (1992).

(List continued on next page.)

*Primary Examiner*—Nita Minnifield
*Assistant Examiner*—Padma Baskar
*Attorney, Agent, or Firm*—Antoinette F. Konski; Baker & McKenzie

[57] ABSTRACT

The present invention provides a method for targeting toxic antimetabolites to gram negative infections. It provides a means of taking advantage of a key disease resistance mechanism to activate these drugs locally, and to overcome the resistance phenotype of the microbes. The invention further provides a method for selecting for antibiotic sensitivity, since a likely mechanism by which organisms are likely to gain resistance to the prodrugs is via loss of enzyme activity, which will make the bacteria sensitive to antibiotics once again.

1 Claim, 1 Drawing Sheet

OTHER PUBLICATIONS

Mobashery, S. et al., "Conscripting β–Lactamase for Use in Drug Delivery, Synthesis and Biological Activity of a Cephalosporin $C_{10}$–Ester of an Antibiotic Peptide" *J. Am. Chem. Soc.* 108:1685 (1986).

Murray, B.E., "Antibiotic Resistance" *Adv. Int. Med.* 42:339–367 (1997).

Rodrigues, M.L. et al., "Synthesis and β–lactamase–mediated activation of a cephalosporin–taxol prodrug" *Chemistry & Biology* 2:223–227 (1995).

Smyth, T.P., "S-Aminosulfeniminopenicillins: Multimode β–Lactamase Inhibitors and Template Structures for Penicillin–Based β–Lactamase Substrates as Prodrugs" *J. Org. Chem.* 63:7600–7618 (1998).

Steinberg, J.P. et al., "Nosocomial and Community–Acquired *Staphylococcus aureus* Bacteremias from 1980 to 1993: Impact of Intracascular Devices and Methicillin Resistance" *Clin. Infect. Dis.* 23:255–259 (1996).

Stosor, V. et al, The Management and Prevention of Vancomycin–Resistant Enterococci *Infect Med* 13(6):487–488, 493–498 (1996).

Straus, S.E., "Strategies To Combat Viral Infections" in: Microbial Disease, $3^{rd}$ Edition, Schaechter et al., eds., Williams & Wilkins, Baltimore, MD, Chapter 43, pp. 403–411 (1998).

Takasuka, T. et al., "Variation in Morphotype, Karyotype and DNA Type of Fluconazole Resistant *Candida albicans* from an AIDS Patient" *J. Infection* 36(1):57–62 (1998).

Vrudhula, V.M. et al., "Cephalosporin Derivatives of Doxorubicin as Prodrugs for Activation by Monoclonal Antibody–β–Lactamase Conjugates" *J. Med. Chem.* 38:1380–1385 (1995).

Bush, K., "β–Lactamase Inhibitors from Laboratory to Clinic" *Clin. Microb. Rev.* 1(1):109–123 (1988).

Kondo, H. et al., "Studies on Prodrugs. 7. Synthesis and Antimicrobial Activity of 3–Formylquinolone Derivatives" *J. Med. Chem.* 31:221–225 (1988).

Mobashula, S. and Johnston, M., "Reactions of *Escherichia coli* TEM β–Lactamase with Cephalothin and with $C_{10}$–Dipeptidyl Cephalosporin Esters" *J. Biol. Chem.* 261(17):7879–7887 (1986).

APPLICATION OF ENZYME PRODRUGS AS ANTI-INFECTIVE AGENTS

CROSS-REFERENCE TO RELATED APPLICATIONS

This application claims priority pursuant to 35 U.S.C. § 119(e) of U.S. provisional application number 60/068,703, filed Dec. 23, 1997, the contents of which are hereby incorporated by reference into the present disclosure.

TECHNICAL FIELD

The present invention relates to the field of drug therapy and specifically to substrates of enzymes which are expressed by infectious agents and which thereby block efficacy of currently available drugs.

BACKGROUND

Throughout this disclosure, various publications are referenced by first author and date, within parenthesis, patent number or publication number. The complete bibliographic reference is given at the end of the application, immediately preceding the claims. The disclosures of these publications are hereby incorporated by reference into this disclosure to more fully describe the state of the art to which this application pertains.

Resistance to antimicrobial agents is a recognized medical problem (Schaechter, et al., 1993; Murray, 1997). The problem was recognized early as penicillin resistance in staphylococci, and is now a recognized problem for the treatment of many bacterial infections, including essentially all nosocomial (hospital-acquired) bacterial infections (Bush, 1988; Steinberg, et al. 1996; Murray, 1997). Nosocomial infections occur in 5% of patients admitted to the hospital (about 2 million patients per year in the United States); they cause an estimated 20,000 deaths per year, and contribute to an additional 60,000 hospital deaths. It is estimated that nosocomial infections add about 7.5 million hospital days and $1 billion dollars in health care costs each year (Wilson, et al. 1991). The importance of antibiotic resistant bacteria has increased as many organisms, e.g., staphylococcus aureus, have developed resistance to several distinct antibiotics (the "multi-resistant" phenotype). The enzymes involved in drug resistance include the penicillinases, β-lactamases, cephalosporinases, and others. These enzymes inactivate antibiotics by modifying them to inactive compounds. Resistance caused by enzymes also includes antibiotic modification by choramphenicol acetyl-transferases and other aminoglycoside modifying enzymes (Murray, 1997). Other mechanisms which contribute to antibiotic resistance include drug permeability mutations, expression of transport proteins that actively extrude antibiotics from target organisms, and mutations in the drug targets themselves (Murray, 1997).

Characteristics of Antibiotics

Antibiotics are drugs which have cytostatic or cytotoxic effects on target organisms. The key to success for an antibiotic is selectivity for the disease target, and lack of toxicity to the host, or patient. Many antibiotics are purified from cultures of microbial organisms themselves, while others are synthetic derivatives of naturally produced antibiotics (Wilson, et al. 1991). The most useful antibiotics against infections are those which attack a microbe-specific target. For example, β-lactam antibiotics interfere with cell wall synthesis by binding to cell wall precursors. Since mammalian cells lack the cell walls of bacteria, these drugs have a tremendous margin of safety for the patient. The most common form of resistance to β-lactam antibiotics is the production of β-lactamases, which degrade the antibiotic molecule. The β-lactamases are encoded by either plasmid or chromosomal genes. In gram-positive bacteria, like staphylococci, the enzymes are exoenzymes, while in most gram-negative bacteria the enzyme is secreted into the periplasmic space (between the bacterial cell membrane and the cell wall).

Although inactivation of antibiotics is probably the most common mechanism for drug resistance, resistance also occurs as a result of mutations in the drug targets themselves. The best characterized of these are mutations in the penicillin-binding-proteins (PBPs), leading to a decrease or loss in the binding. The β-lactam antibiotics include penicillin, ampicillin, carbenicillin, and the cephalosporins (including cephalexin, cefaclor, cefoxitin, cefotaxime and cefoperazone). Because resistance is very common via production of high levels of β-lactamases, new drugs have been developed to inhibit these enzymes, thereby increasing the efficacy of the β-lactam antibiotics. Examples of β-lactamase inhibitors include clavulanate, timentin and sulbactam (Bush, 1988; Wilson, et al. 1991; Schaechter, et al. 1993). The combination of β-lactam antibiotic with β-lactamase inhibitor has extended the useful pharmacologic lifetimes of these antibiotics (Bush, 1988).

Drawbacks of Current Antimicrobial Agents.

Current agents have well characterized targets of action. Several examples are given below:

| Antibiotic Family | Example | Target |
|---|---|---|
| β-lactam antibiotics | Penicillins, cephalosporins | Cell wall biosynthesis |
| Sulfonamides | Sulfanilamide | Blocks synthesis of tetrahydrofolate |
| Aminoglycosides | Streptomycin | Protein synthesis |
| Trimethoprim | — | Folate metabolism |
| Chloramphenicol | — | Protein synthesis |
| Vancomycin | — | Cell wall synthesis |

Other antibiotics work by blocking DNA replication, production of cellular RNA, or by modification of multiple cellular targets (Schaechter, et al. 1993). The occurrence of resistance to antibiotics is commonplace, and many of the mechanisms have been described (Schaechter, et al. 1993; Murray, 1997). These mechanisms include overexpression of the target enzyme, expression of an antibiotic inactivating enzyme, or mutation of the target so that it is no longer recognized by the antibiotic. Examples of these are given below:

| Antibiotic | Principle mechanism of resistance |
|---|---|
| Penicillins and other β-lactam antibiotics | Inactivation by β-lactamase |
| Sulfanilamide | Mutation of dihydropteroate synthase target enzyme |
| Aminoglycosides | Inactivation by aminoglycoside modifying enzyme, or by target mutation |
| Trimethoprim | Mutation of dihydrofolate reductase target enzyme |

-continued

| Antibiotic | Principle mechanism of resistance |
|---|---|
| Chloramphenicol | Inactivation by chloramphenicol transacetylase |
| Methicillin | Mutation of penicillin binding proteins |
| Vancomycin | Mutation in target cell wall peptide |

Increased resistance of bacterial infection to treatment with antibiotics has been carefully documented (see e.g., Steinberg, et al. 1996), and has now become a generally recognized problem (Murray, 1997). Each emergence of resistance to the "new" antibiotic derived from its previous generation (e.g., cephalosporin from penicillin) has been met with initial success, and then increasing reports of resistance. The progression of β-lactamases antibiotics is typical of the field. Each successive antibiotic is more resistant to degradation by β-lactamase, and the organism then produces larger amounts of the β-lactamase. This is especially a problem for nosocomial (hospital) acquired infections (Wilson, et al. 1991; Murray, 1997). The most common mechanism for transmission of the drug resistance phenotype is via plasmid, although some modulators of antibiotic resistance are located on the bacterial chromosome (Schaechter, et al. 1993). The despair of the medical community has been addressed by the production of inhibitors of the β-lactamases. Unfortunately, although the β-lactamases have very much overlapping substrate specificities, they have evolved differently to have distinct, but related, amino acid sequences. This problem is expressed by the widely varying efficacies of each β-lactamase inhibitor for different enzymes. In addition, the new generation antibiotics are usually more toxic than their predecessors, and cannot be administered to patients in a convenient way. For example, vancomycin, often called the "antibiotic of last resort," has toxicity which prevents its use except in the most dangerous, multiply drug-resistant, infections (Physicians Desk Reference 1996). A cycle of drug resistance has been established which requires a new approach to resolve. Therefore, a need exists for a new generation of antibiotics which are not susceptible to the established drug-evasion mechanisms. This invention satisfies this need and provides related advantages as well.

SUMMARY OF THE INVENTION

Many enzyme-prodrug combinations have been described in detail. Applications have included antiviral drugs like gancyclovir (Straus, 1993) and antibody or gene directed expression of bacterial enzymes to treat cancer (Melton, et al. 1996; Stosor, et al. 1996). The current invention redirects this technology to treat infectious disease resistant to therapy by antibiotics.

Thus, this invention provides a method for identifying potential therapeutic agents useful to kill an antibiotic resistant gram negative microorganism by contacting a sample with a candidate therapeutic agent that is a selective substrate for an enzyme which is overexpressed and confers antibiotic resistance to the microorganism under conditions that favor the activation of the agent by the enzyme and assaying the sample for inhibition of proliferation of the microorganism.

This invention also provides a method for selectively inhibiting the proliferation of an antibiotic resistant gram negative microorganism, by contacting a sample containing the microorganism with an effective amount of a prodrug that is selectively converted to a toxin by the resistance enzyme itself. In one embodiment, the most expedient method for organisms to develop resistance to this new antibiotic is by losing expression of β-lactamase. This invention therefore provides a method for causing antibiotic resistant organisms to regain sensitivity to the original antibiotics.

DESCRIPTION OF THE FIGURE

The FIGURE depicts a prodrug useful in the practice of this invention.

MODES FOR CARRYING OUT THE INVENTION

Figure 1:
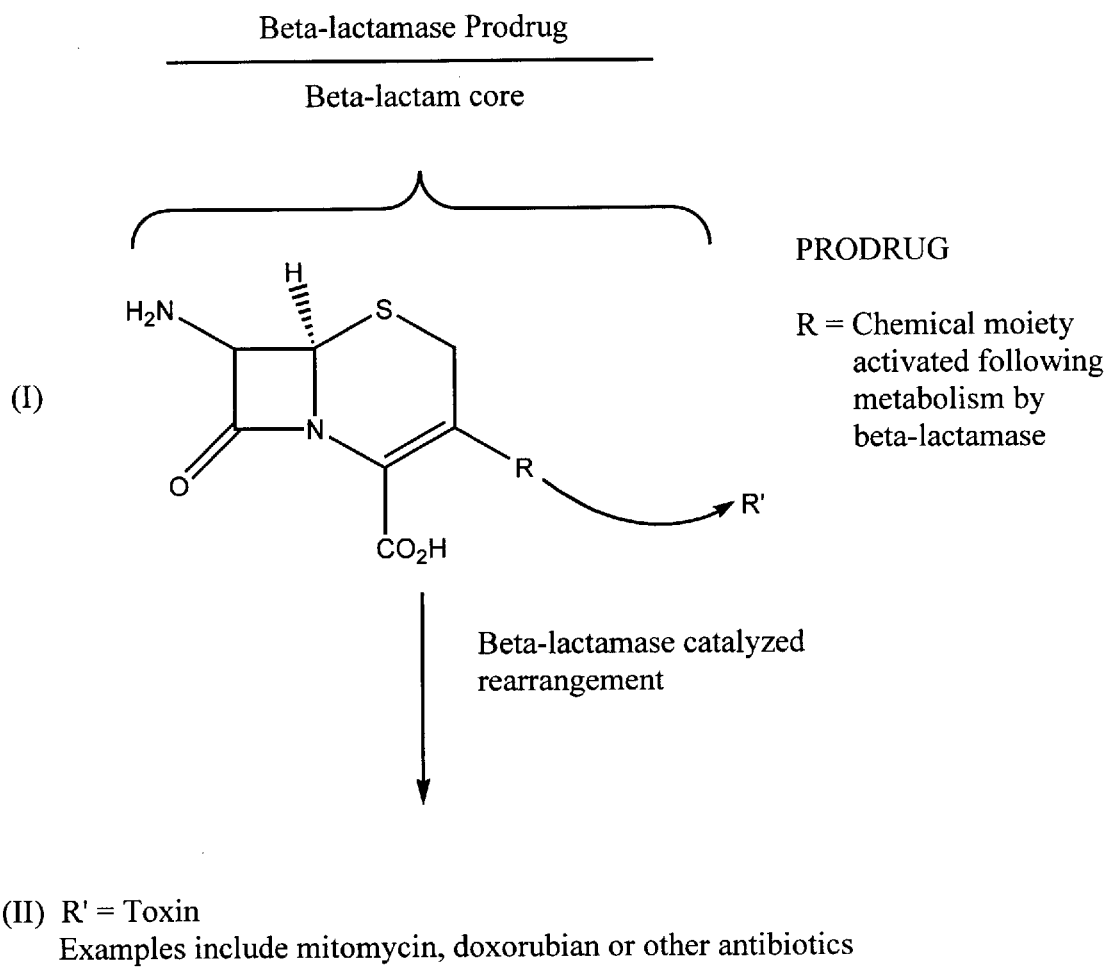

The present invention provides a method for targeting toxic antimetabolites to gram negative infections. It enables these antibiotics for use outside of the anticancer field, to which these molecules and their derivatives have been limited as a result of their toxicity. In one embodiment, the invention provides a means of taking advantage of a key disease resistance mechanism, the overproduction of β-lactamase, to activate these drugs locally (within the periplasm of the gram negative bacterium), and to overcome the resistance phenotype of the microbes. The invention further provides a method for selecting for β-lactam antibiotic sensitivity, since a likely mechanism by which organisms are likely to gain resistance to the prodrugs is via loss of β-lactamase activity, which will make the bacteria sensitive to β-lactam antibiotics once again. Thus, this invention provides a method of reversing antibiotic resistance in a microorganism by selecting for loss of the activity of the resistance enzyme. The method requires contacting the microorganism with a prodrug metabolized by the resistance enzyme thereby killing the microorganisms expressing the resistance enzyme. Only the organisms having lost the resistance enzyme will survive. These surviving organisms now are selected for sensitivity to the original antibiotic and can be effectively killed by contacting them with the original antibiotic. In this way, the invention also provides a combination therapy for the treatment of microbial infections, wherein the microorganism is capable of developing antibiotic resistance as defined below. The combination therapy requires first treating with the antibiotic, then treating with a prodrug as defined herein, and then finally, treating with the original antibiotic. Also claimed is a method for reversing antibiotic resistance in a microorganism by contacting the microorganism with an effective amount of an agent that is a selective substrate for an enzyme which is overexpressed and confers antibiotic resistance to the microorganism.

In one embodiment, the current invention employs drugs with the general structure of β-lactam derived chemotherapeutic antibiotics for treatment of infectious disease. Unlike the previous work (Melton & Sherwood, 1996), no combination with a targeting agent is needed. The prodrugs are utilized directly for topical or systemic therapy of bacterial infections.

This invention provides a method for identifying potential therapeutic agents useful to kill an antibiotic resistant gram negative microorganism, by contacting a sample containing the antibiotic-resistant microorganism with a candidate prodrug that is a selective substrate for an enzyme which is overexpressed and confers drug resistance to the infecting microorganism. As used herein the term "prodrug" means a precursor or derivative form of a pharmaceutically active agent or substance that is less cytotoxic to a target cell as compared to the drug metabolite and is capable of being enzymatically activated or converted into the more active form.

The prodrug is contacted with the sample under conditions that favor the activation of the prodrug by the enzyme and then assaying the sample for inhibition of microbial proliferation of the infected cells in the sample as compared to a control cell. Varying concentrations of the potential agent are contacted with the sample to determine the optimal effective concentration of the agent. Thus, in one aspect, this invention relates to the discovery and use thereof of agents which are selective substrates for enzymes that confer drug resistance to microorgansims.

Kits containing the agents and instructions necessary to perform the screen and in vitro method as described herein also are claimed.

Samples of cells or tissues as used herein encompass cells or tissues characterized by the presence of drug resistance, the drug resistance being the result of the overexpression of an enzyme by the infecting microorganism. The cell can be a eucaryotic cell, i.e., a mammalian cell, e.g. a mouse cell, a rat cell, a hamster cell, or a human cell. The cell also can be a procaryotic cell such as a yeast or bacterial cell. The cell can be continuously cultured or isolated from an infected animal or human subject.

The method can be practiced in vitro, ex vivo or in vivo. In vivo practice of the invention in an animal such as a rat or mouse provides a convenient animal model system which can be used prior to clinical testing of the therapeutic agent or prodrug. In this system, a potential prodrug will be successful if microbial load is reduced or the symptoms of the infection are ameliorated, each as compared to an untreated, infected animal. It also can be useful to have a separate negative control group of cells or animals which has not been infected, which provides a basis for comparison.

When practiced in vivo, the candidate prodrug is administered to the animal in effective amount. As used herein, the term "administering" for in vivo and ex vivo purposes (if the target cell population is to be returned to the same (autologous) or another patient (allogeneic)) means providing the subject with an effective amount of the candidate prodrug effective to reduce bacterial load. In these instances, the agent or prodrug may be administered with a pharmacuetically acceptable carrier. The agents and compositions of the present invention can be used in the manufacture of medicaments and for the treatment of humans and other animals by administration in accordance with conventional procedures, such as an active ingredient in pharmaceutical compositions.

Methods of administering pharmaceutical compositions are well known to those of skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the prodrug used for therapy, the purpose of the therapy, the microorganism being treated, the severity of the infection, and the subject being treated. Single or multiple administrations can be carried out with the dose level and pattern being selected by the treating physician. For example, the compositions can be administered to a subject already suffering from an antibiotic resistant bacterial infection. In this situation, an effective "therapeutic amount" of the composition is administered to prevent continued and to at least partially arrest microbial growth and proliferation and ameliorate the symptoms associated with infection.

However, the prodrugs can be administered to subjects or individuals susceptible to or at risk of developing an infection. In these embodiments, a "prophylactically effective amount" of the composition is administered to maintain cell viability and function at a level near to the pre-infection level.

It should be understood that by preventing or inhibiting unwanted cell death in a subject or individual, the prodrug compositions and methods of this invention also provide methods for treating, preventing or ameliorating the symptoms associated with a disease characterized by unwanted infection. Such diseases include but are not limited to gram-negative infections, as shown in the table below.

| Organism | Disease(s) |
| --- | --- |
| Neisseria | Gonorrhea, meningitis, septicemia |
| Salmonella | Typhoid fever, food poisoning |
| Shigella | Bacillary dysentery |
| Haemophilis | Pneumonia, meningitis |
| Bacteriodes | Peritonitis |

Amplification of genes associated with microbial resistance can be detected and monitored by a modified polymerase chain reaction (PCR) as described in Takasuke, T. et al. 1998 or U.S. Pat. No. 5,085,983. Alternative assays include enzyme activity assays Miller, 1992; Spector, et al. 1997 and via the polymerase chain reaction (Spector, et al. 1997 and Maher, et al. 1995).

This invention also provides a method for selectively inhibiting the proliferation of an antibiotic resistant gram negative microorganism, by contacting the microorganism with an effective amount of a prodrug that is selectively converted to a toxin in the microorganism by an enzyme, the overexpression of the enzyme conferring the antibiotic resistance to the microorganism. As noted above, the contacting can be accomplished in vitro against cultured or sampled cell samples, ex vivo, or in vivo in an animal system. The methods of this invention also can be practiced ex vivo using a modification of the method described in U.S. Pat. No. 5,399,346.

In one embodiment, the microorganism is resistant to a β-lactamase antibiotic, e.g., penicillin or cephalosporin.

β-lactamases can be found either extracellularly or within the periplasmic space of the microorganism. In general, active β-lactamases from gram-positive bacteria are excreted into the medium. β-Lactamase activity in gram-negative organisms is found primarily in the periplasmic space, although some leakage of enzyme into the medium can occur. Genetic information for β-lactamase synthesis either can be carried on a plasmid or can occur within the bacterial chromosome; either of these can result in the production of enzymes leading to resistance to the common β-lactam antibiotics.

Plasmid-mediated β-lactamases are especially insidious because of the ease with which these extrachromosomal elements can be transferred from one bacterial strain to another. Some β-lactamases, initially coded for on a plasmid, can have this genetic information eventually incorporated into the chromosome as a permanent addition to the cellular deoxyribonucleic acid. It is not unusual for bacteria to carry multiple plasmids, coding for multiple antibiotic-modifying enzymes. It is also possible that multiple resistance factors can be carried on a single plasmid. Thus, it is becoming common for bacteria to appear with resistance to two or three classes of antibiotics.

One of the most troubling aspects of chromosomal β-lactamase production is; the ease of inducibility of these enzymes, resulting in high concentrations of β-lactamase. The best inducers known are β-lactamase antibiotics, frequently those that are subsequently hydrolyzed by the induced enzyme. In some cases a stably derepressed mutant may be selected, with total β-lactamase content representing as much as 4% of the total protein in the bacterial cell.

Suitable prodrugs which are activated by β-lactamase include, but are not limited to cytoxic molecules selected from the group consisting of mitomycins, adriamycin, doxorubicin, and nitrogen mustard. In one particular embodiment, the prodrug has the formula:

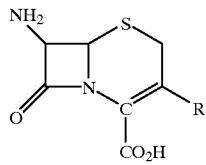

wherein R is a structure derived from chemical synthesis, optimized by testing against gram-negative bacteria in vitro and in vivo. Following activation by β-lactamase, R is converted to a cytostatic or cytotoxic drug (referred to in the FIGURE as R'). In one embodiment, R' is an agent capable of exerting a cytotoxic effect on infectious cells such as bacteria, which overexpress β-lactamase when released from a cephalosporin-prodrug.

As is known to those of skill in the art, using a modification of the teachings of U.S. Pat. Nos. 5,549,974; 5,639,603 and 5,679,773, the prodrugs as shown herein are synthesized and assayed for biological activity using the methods of this invention.

The cytotoxic compound is one having at least one functional group amenable to chemical modification to provide the β-lactam prodrug mechanism of action. Generally, such functional groups are selected from amino, carboxyl, and hydroxyl groups such that the linkage between the cytotoxic agent and the β-lactam component is of the carbamate, amide, ester, and carbonate types.

Synthesis of these prodrugs, and some potential derivatives, are described in the following European Pat. Publications: 0 317 956 (Application number 88119418.7), 0 484 870 A2 (Application number 91118822.5), 0 302 473 B1 (Application number 88112646.0), EP 0 742 015 A1 (Application number 96106146.2), EP 0 745 390 A2 (Application number 96108570.1). These structures and methods of synthesis are well known in the art and are incorporated by reference. This includes but is not limited to β-lactam prodrugs derived from the mitomycins, adriamycin/doxorubicin, nitrogen mustards, or other cytotoxic molecules with similar structures which allow derivatization by the β-lactam substituent to allow activation and bacterial cell killing. This general structure may be appropriately modified, for example, using combinatorial chemistry, or by other methods well known in the art.

In one embodiment, the derivatives will have the general structure:

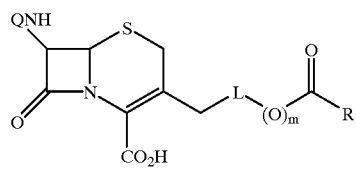

wherein Q is hydrogen, an amino protecting group conventionally used in cephalosporin synthesis, or the acyl group of a known 7-acylaminocephalosporin antibiotic; L is a direct bond or —S—$(CH_2)_n$—; R is an agent capable of exerting a cytotoxic effect on cells when released from said cephalosporin-prodrug; n is 2, 3 or 4; and m is 0 or 1 with the proviso that when L is a direct bond, m is 1; or a pharmaceutically acceptable salt thereof.

For the purpose of the present invention, the nature of the substituent Q is not critical as the cephalosporin moiety serves as a carrier of the cytotoxic drug and does not contribute to the therapeutic effect of the cytotoxic drug. Thus, Q may be, for example, hydrogen, a protecting group commonly used in cephalosporin chemistry, or a substituent of known cephalosporin antibiotics. Examples of the latter include, but are not limited to, phenylacetyl, 2-thionylacetyl, a-hydroxyphenylacetyl, phenylglycyl, p-hydroxyphenylglycyl, and (2-amino-4-thiazolyl) (methoxylmino)acetyl.

In another embodiment, the cytotoxic compound is one having at least one functional group amendable to chemical modification to provide the cephalosporin prodrug. Generally, such functional groups are selected from amino, carboxyl, and hydroxyl groups such that the linkage between the cytotoxic agent and the cephalosporin component is of the carbamate, amide, ester, and carbonate types.

This invention also claims compounds having the above structure, derivatives, and pharmacuetically effective salts thereof, and medicaments containing the same. The compounds may be used alone or in combination with an acceptable carrier, such as pharmaceutically acceptable carriers. The compounds also can be combined with other therapeutic agents for use in combination therapy. Processes for producing the compounds also are within the scope of this invention.

It is one of the aims of this invention to provide prodrugs which can be activated by any β-lactamase, thereby avoiding the problem of selecting the proper β-lactamase inhibitor. Because the β-lactam adduct of the prodrug will be broadly activated by β-lactamases of many species of bacteria (see, e.g., Vrudhula, et al. 1995), a single prodrug will find utility for treating many different kinds of infections, previously resistant to treatment because of high levels of β-lactamase production by the target organism. This approach avoids the problem of mutation resistance encountered with β-lactamase inhibitors (Bush, 1988). This approach is also useful because resistance to these prodrugs is likely to come about via the loss of β-lactamase activity. This will result in the bacterium regaining sensitivity to the penicillins. This invention therefore also claims a method for causing β-lactam antibiotic resistant organisms to become sensitive to β-lactam antibiotics.

Another limitation of some currently available potent antibiotics is their lack of specificity. Examples include mitomycin and doxorubicin, both isolated from Streptomyces. One of the major challenges in drug discovery and development is efficient targeting of the drug to a disease mechanism, with lack of effect on non-diseased, or host organs. Because many of the antibiotics which have been discovered to date do not have good discrimination between bacterial and host targets, they have not been employed as antiinfective agents. Some of these compounds have, however, been employed to treat other diseases, such as cancer. This invention provides a means of targeting these toxic compounds (in the form of the prodrug) to the infectious organism with minimal exposure of the host to the toxin.

Also relevant to this invention is the considerable prior art in which prodrug, constructs of these antibiotics have been designed in which they are activated by bacterial specific enzymes, such as β-lactamase. In this technology, known as antibody directed prodrug therapy (ADEPT) or gene directed prodrug therapy (GDEPT), a bacterial enzyme is localized to a tumor via a specific targeting agent, such as an antibody (Melton & Sherwood, 1996). The prodrug is then administered to the patient, and is activated preferentially at the tumor site (where the enzyme has been localized via its conjugation to antibody). This provides a localization of the antitumor antibiotic, allowing higher concentrations of the active drug at the tumor site, and less systemic exposure to the active drug and its toxic activities. Several prodrugs have been prepared which are broadly activated by β-lactamases. These include β-lactam derivatives of doxorubicin (Vrudhula, et al. 1995), paclitaxil (Rodrigues, et al. 1995), nitrogen mustards (Kerr, et al. 1995), vinca alkaloids (Meyer, et al. 1992), and mitomycin (Vrudhula, et al. 1995). These compounds have been shown to be activated by a broad spectrum of β-lactamases from different bacterial species (Vrudhula, et al. 1995). The effectiveness of these drugs is dependent upon proper localization of the activating enzyme via antibody binding to tumor, or by preferential expression of the activating enzyme in tumor cells. The authors of the publications cited above do not disclose the utility of the prodrugs as anti-infectious agents. This invention requires no such localization by antibody or other methods because only the infectious organism is expressing the activating enzyme. This invention focuses on gram negative organisms, in which the β-lactamase localizes in the periplasmic space. It is likely that for gram-positive organisms, in which the β-lactamase is excreted, that the desired localization of active toxin would not be accomplished.

It is the purpose of the current invention to take advantage of this prodrug technology to treat infectious disease, not cancer. Similar prodrugs, activated by β-lactamase or other microbial enzymes normally involved in resistance to antibiotic therapy, either expressed solely by the infectious agent and/or overexpressed by the infectious agent, will be used to activate prodrug versions of normally host-toxic drugs specifically to treat infections. This "biochemical targeting" technology overcomes the lack of specificity of action of the drugs described above by having the activated forms created at high concentrations only within or at the sites of infectious disease. This is a novel approach and enables the use of drugs previously too toxic for use against infectious disease. Previously, Mobashery and colleagues (Mobashery, et al. 1986; Mobashery and Johnson, 1986) described a polypeptide antibiotic that appeared to be activated by β-lactamase. Their work failed to address several important issues: (1) Activity was dependent not only on β-lactamase expression, but also upon transport of the peptide into the bacterial cell by peptide permeases, and subsequent intracellular activation by other cellular enzymes; (2) The peptide used was not active in an "enriched" medium (Boisvert, et al. 1986). The first limitation means that access of the drug, and subsequent efficacy, was limited by its ability to enter the cell. Secondly, the peptide lacked activity in enriched medium, which is likely to be the situation encountered in any in vivo application. The authors do not anticipate enabling the use of the more toxic antibiotics (such as mitomycin or doxorubicin) as a result of this "targeting" approach. Similarly, the groups working on ADEPT, while recognizing value in the application of β-lactam prodrugs to treat cancer, did not recognize their use in infectious disease.

The antibiotics will be tested on gram negative bacteria grown in liquid or solid media, supplemented with the candidate prodrug according to well established methods (Miller, 1992). In order to test efficacy in vivo, mice will be infected with β-lactamase producing gram negative bacteria and, once the infection is established, will be treated with β-lactam antibiotic versus β-lactam prodrug. Disease progression will be monitored by counting live bacteria in samples taken from the mice. The goal of this experiment is to prove the safety of the drugs in vivo, establish their efficacy, and estimate dosages for use in humans.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the agent through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the, present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a stolid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

These agents of this invention and the above noted compounds and their derivatives may be used for the preparation of medicaments for use in the methods described herein.

In the clinical use of the prodrug antibiotics will likely follow well established guidelines. Dosage will likely be similar to those already employed for most other antibiotics. It is estimated that a dose of prodrug will be in the range of 100 mg to 1 gm, given once every eight hours, or once a day, for one or two weeks, or until the patient tests negative for infectious organisms.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

REFERENCES

Boisvert, W. et al. *J Biol. Chem.* 260:7871–7878.

Bush, *Clinical Microbial Rev.* 1:109–123 (1988).

Kerr, D. E. et al. *Cancer Research* 55:3558–3563 (1995).

Maher, M. et al. *Mol. Cell Probes* 9:265–276 (1995).

Melton, R. G. and Sherwood, R. F. *J Natl. Cancer Inst.* 88:153–65 (1996).

Meyer, D. L. et al. *Bioconjugate Chem.* 3:42–48 (1992).

Miller, J. H. A Short Course In Bacterial Genetics: A Laboratory Manual And Handbook For *E.Coli* And Related Bacteria. Cold Spring Harbor Press (1992).

Mobashery, S. et al. *J Am. Chem. Soc.* 108:1685.

Mobashery and Johnson, *J Biol. Chem.* 261(17): 7879–7887.

Murray, B. E. Antibiotic Resistance, in *Adv. Int. Med.* 42:339–367 (1997).

Physicians Desk Reference, $50^{th}$ Edition (1996) Publ. Medical Economics Co., Montvale, N.J.

Rodrigues, M. L. et al. *Chemistry And Biology* 2:223–227 (1995).

Schaechter et al. Mechanisms of microbial disease ($2^{nd}$ Ed). Publ. Williams & Wilkins. pp.973 (1993).

Spector, (1997) A Laboratory Manual, Vol. I–III, Cold Spring Harbor Press.

Steinberg, J. P. et al. *Clinical Infectious Diseases* 23:255–259 (1996).

Stosor, V. et al. *Infect. Med.* 13:487–488 (1996), Opit. Pp. 493–498 (1996).

Straus, S. E., Strategies To Combat Viral Infections, In Mechanisms Of Microbial Disease ($2^{nd}$ Ed.). Ed. T. S. Satterfield, Publ. Williams & Williams, Baltimore., Md. pp. 537–550, 973 (1993).

Takasuka, T. et al. J. Infect. 36(1):57–62.

Vrudhula, V. M. et al., *J Med. Chem.* 38:1380–1385 (1995).

Wilson J. D., Braunwald E, Isselbacher K. J., et al. Harrison's Principles of Internal Medicine. ($12^{th}$ Ed). Publ: McGraw-Hill pp. 2208 (1991).

U.S. Pat. No. 5,549,974
U.S. Pat. No. 5,639,603
U.S. Pat. No. 5,679,773
European Pat. Publication No. 0 317 956
European Pat. Publication No. 0 484 870
European Pat. Publication No. 0 302 473
European Pat. Publication No. 0 742 015
European Pat. Publication No. 0 745 390

What is claimed is:

1. A method for reversing antibiotic resistance in a microorganism, the method comprising contacting the microorganism with an effective amount of an agent wherein said agent is a selective substrate for an enzyme and which is activated by the enzyme into a toxin, and the enzyme being overexpressed and which confers antibiotic resistance to the microorganism.

* * * * *